United States Patent
Berier et al.

(10) Patent No.: US 7,221,824 B2
(45) Date of Patent: May 22, 2007

(54) MINIATURIZED FOCUSING OPTICAL HEAD IN PARTICULAR FOR ENDOSCOPE

(75) Inventors: Frederic Berier, Courbevoie (FR); Stephane Bourriaux, Champs sur Marne (FR); Magalie Genet, Paris (FR); Bertrand Viellerobe, Vincennes (FR); Alexandre Loiseau, Paris (FR); Benjamin Abrat, Paris (FR)

(73) Assignee: Mauna Kea Technologies, Paris (FR)

( * ) Notice: Subject to any disclaimer, the term of this patent is extended or adjusted under 35 U.S.C. 154(b) by 513 days.

(21) Appl. No.: 10/499,987

(22) PCT Filed: Dec. 20, 2002

(86) PCT No.: PCT/FR02/04482

§ 371 (c)(1),
(2), (4) Date: Jun. 24, 2004

(87) PCT Pub. No.: WO03/056379

PCT Pub. Date: Jul. 10, 2003

(65) Prior Publication Data

US 2005/0157981 A1    Jul. 21, 2005

(30) Foreign Application Priority Data

Dec. 28, 2001   (FR) .................... 01 16979

(51) Int. Cl.
*G02B 6/32* (2006.01)
*G02B 6/06* (2006.01)
*G02B 27/02* (2006.01)

(52) U.S. Cl. .................... 385/33; 385/117; 385/119; 359/800

(58) Field of Classification Search ..................... None
See application file for complete search history.

(56) References Cited

U.S. PATENT DOCUMENTS

| 5,191,879 A | 3/1993 | Krauter |
| 5,961,445 A | 10/1999 | Chikama |
| 5,974,211 A * | 10/1999 | Slater .................... 385/33 |
| 6,470,124 B1 | 10/2002 | Le Gargasson et al. |

FOREIGN PATENT DOCUMENTS

| EP | 0 821 907 | 2/1998 |
| EP | 0 887 043 | 12/1998 |
| EP | 1 157 655 | 11/2001 |
| WO | WO 99/47041 | 9/1999 |
| WO | WO 00/16151 | 3/2000 |

* cited by examiner

*Primary Examiner*—Rodney Bovernick
*Assistant Examiner*—Omar Rojas
(74) *Attorney, Agent, or Firm*—Young & Thompson

(57) ABSTRACT

An optical head for equipping the distal end of a flexible optical fiber bundle, designed to be urged into contact with an analyzing surface and including optical elements for focusing an excitation signal into a so-called excitation focal point located at a specific depth beneath the analyzing surface and for sampling a signal backscattered by the excitation focal point which is carried back by the fiber bundle. The head includes an optics-holder tube wherein are inserted on one side the distal end portion of the fiber bundle and on the other optical elements, the latter including a plate placed in contact with the end of the fiber bundle whereof the index is close to that of the fiber core and a focusing optical block, an output window being further provided adapted to provide index adaptation so as to eliminate parasitic reflection occurring on the analyzing surface.

22 Claims, 3 Drawing Sheets

MINIATURIZED FOCUSING OPTICAL HEAD IN PARTICULAR FOR ENDOSCOPE

BACKGROUND OF THE INVENTION

1. Field of the Invention

The present invention relates to a miniaturized optical head provided for equipping the distal end of a flexible optical fibre bundle, said head being intended to be placed in contact with an analyzing surface and adapted for focussing an excitation signal conveyed by said fibre bundle into an excitation focal point which can be situated at different depths relative to the contact surface of the head. The optical head is also adapted for collecting a backscattered signal originating from the subsurface excitation focal point in order for it to be carried by the fibre bundle in particular to detection means and means of analysis and digital processing of the signal.

The fields of application concerned are subsurface analysis devices which are confocal in character, the signals conveyed being in particular those of the field of imaging and/or spectroscopy, depending on the source or sources of excitation and detection means used. The confocal character results from the use of the same fibre or fibres for conveying the excitation signal and the backscattered signal. The device can be used for in situ biological analyses, on humans or animals, external, for example in the field of dermatology, or internal and accessible using the instrument channel of an endoscope into which the optical fibre bundle and the optical head can be introduced. It can also be used for cell analyses carried out ex vivo on samples. Moreover also, the optical head can be used for analyzing the interior of a manufactured device.

At present, the medical fields of gastroenterology, respirology, gynaecology, urology, otorhinolaryngology, dermatology, ophthalmology, cardiology and neurology are concerned.

The magnification of the optical head according to the present invention may or may not be unitary. It is the analysis and signal processing means provided on the side of the proximal end of the optical fibre bundle which allow the restitution of an image or a graph which can be interpreted by a user.

The sought objectives for the optical head are in particular the following:
- to have a minimal space requirement in particular in order to be able to be inserted into the instrument channel of an endoscope which in general possesses a diameter comprised between 2 and 4 mm and a given radius of curvature.
- to provide a good quality backscattered signal in which aberrations are minimized;
- to minimize parasitic reflections at the distal output of the fibre bundle;
- to provide a spatial resolution of the excitation focal point of the order of 4 µm, or even less in the case of a non-unitary magnification, allowing the analysis and/or observation of a tissue at a cellular scale;
- to be able to be brought into contact with the analyzing surface in order to avoid the problems linked with untimely movements; and
- to allow a point focussed in a section plane XY situated at a given depth from the analyzing surface.

Miniaturization of the optical head is also advantageous in order to increase the precision of its positioning and also to minimize mechanical inertia in automated uses, for example in extension of a robot arm or telemanipulator.

2. Description of the Related Art

From the document WO 00/16151, an observation device is known comprising an optical focussing head at the distal end of a flexible channel of optical fibres comprising at the channel output successively three lenses: a ×10 microscope objective, a doublet of 150 mm focal length and a doublet of 50 mm focal length.

An optical head is also known, comprising a system of four lenses, the first lens and the fourth lens being two ×10 microscope objectives and the second and third lenses two doublets of 150 mm focal length constituting an afocal system of magnification 1.

These optical systems have the following major drawbacks:
- this type of construction, based on sophisticated microscope objectives (which can contain up to twelve lenses) cannot be miniaturized in order to be introduced into an endoscope instrument channel with a diameter of 2 to 4 mm;
- the lateral resolution is of the order of 8 µm, insufficient for analyzing a tissue on the cellular scale;
- in the case of confocal imaging, with illumination and scanning of the fibres one by one, a distortion of the image formed is observed ("ballooning" of the lines).

BRIEF SUMMARY OF THE INVENTION

The aim of the present invention is to overcome these drawbacks and to achieve the objectives mentioned above.

This aim is achieved with a miniaturized optical head provided for equipping the distal end of a flexible optical fibre bundle, said optical head being intended to come into contact with an analyzing surface and comprising optical means for focussing an excitation signal coming out of said fibre bundle into a so-called excitation focal point situated at a given depth beneath the analyzing surface and for collecting a signal backscattered by the excitation focal point which is carried back by said fibre bundle, characterized by an optics-holder tube, circular in section, wherein are inserted on one side the distal end portion of the fibre bundle and on the other the optical means, the latter comprising a plate placed in contact with the end of the fibre bundle whereof the index is close to that of the fibre core and a focussing optical block, an output window being moreover intended to come into contact with the analyzing surface and adapted to provide index adaptation in order to eliminate parasitic reflection occurring on the analyzing surface.

The optical block comprises a set of lenses which can be standard, the positioning and the curvature of each lens are not allowing a coupling of the signal reflected by the lenses, in particular a coupling of more of $10^{-5}$ relative to the fibre output signal. This makes it possible to avoid interference being caused to the signal originating from the sample observed by this reflected signal. To this end, each lens constituting the optical block possesses an anti-reflection treatment optimal to the working wavelength, and, moreover, it is placed in an extra-focal plane and has a curvature which allows rejection of the signal reflected outside the excitation fibre. The combination of the various lenses allows illumination of the analysis site as needed point by point whilst ensuring a good optical quality necessary for obtaining a high-resolution confocal image.

According to a first embodiment, the window is also inserted at the end of the optics-holder tube.

According to a second embodiment, allowing analysis at different depths, in particular between 50 and 400 µm, the window is carried by a mobile cap fitted onto the end of the optical head and displaceable using appropriate means, hydraulic, pneumatic, piezo-electric, motorized, electro-optical, etc. the space requirement of which remaining compatible with the miniaturization objective.

Other methods of displacement of the depth of the analysis plane can be envisaged, in particular the axial displacement of a mobile optical means provided in the optical block, this mobile optical means being able to be constituted by a refractive optics (standard or with a gradient index) or a diffractive optics. A piezoelectric motor can carry out the displacement of this mobile optical means. A hydraulic actuator can also be used. Another axial scanning mode can also consist of using an optical means specific to the optical block adapted to change the focal distance by the modification of its radius of curvature (or optical power). This optical means can be for example a liquid optical means.

For the observation and analysis of biological tissues which are highly diffusing and/or have cellular details requiring a very high spatial resolution, such as the nuclei of healthy cells, an optical head will be preferred with non-unitary magnification, in particular of 0.5 from the distal end of the image guide to the analysis plane. This makes it possible to improve the lateral and axial resolution, and to obtain a larger numerical aperture.

Thus, according to the invention, in order to obtain a miniaturization, the microscope objectives conventionally chosen in the focussing heads because of their excellent optical quality are replaced by a combination of mechanical and optical means optimized in order to obtain an optimal coupling of the fibre output signal, i.e. with an optimized transcription of the point spread function (PSF), a wave front quality limited by the diffraction (preferably of the order of $\lambda/30$ at the centre of the field to $\lambda/20$ at the edge of field) in order to thus obtain a minimization of the aberrations due to the use of more standard lenses for the focussing optical block.

For the observation of tissues which are only slightly diffusing and have details greater than 5 µm, in particular for only slightly diffusing biological tissues or manufactured objects such as integrated circuits, a unitary magnification head has the advantage of being simpler to produce and integrate, due to its symmetrical character, and as a result has a lower cost than that of the non-unitary magnification head.

BRIEF DESCRIPTION OF THE SEVERAL VIEWS OF THE DRAWINGS

Other advantages and characteristics of the invention will become clear from the description which follows of a non-limitative embodiment, which description refers to the attached drawing in which.

DETAILED DESCRIPTION OF THE INVENTION

Figure 1:
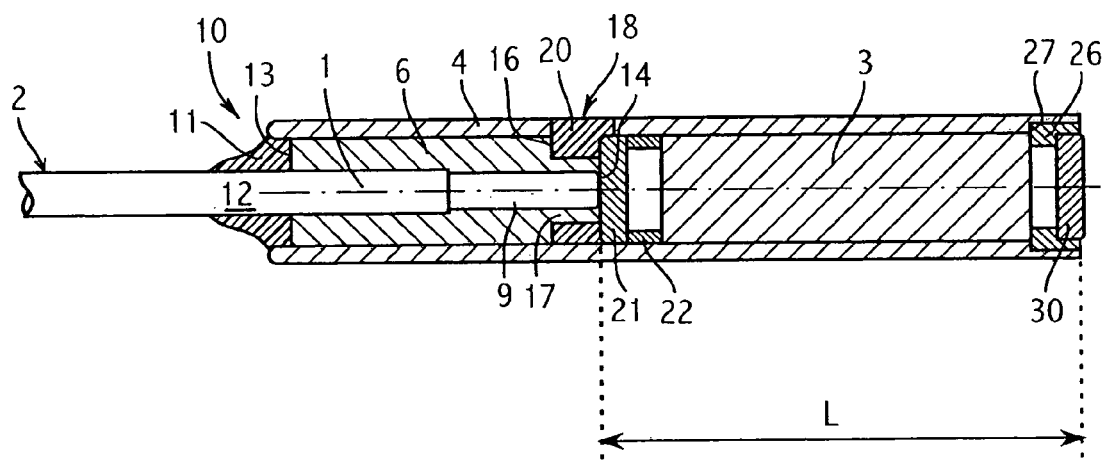
FIG. 1 is an opto-mechanical longitudinal cross-section view of an optical head according to the invention.

According to the embodiment chosen and represented in FIG. 1, the optical head comprises a mechanical structure wherein is introduced and fixed on the one side the distal end portion 1 of a bundle 2 of organized flexible optical fibres and on the other side optical means are accommodated, allowing the focussing of a signal issuing from one or more fibres of said fibre bundle.

The mechanical structure comprises an optics-holder tube 4 which is circular in section. The bundle 2 is constituted by flexible optical fibres which are organised in the same manner at the input and output of the bundle, and surrounded by a sheath 12. A tubular metal joining piece 6 open at either end is coupled and adjusted on the end portion 1 of the bundle 2 in such a manner that the end 14 of the bundle 2 is flush with the end of the joining piece 6. The joining piece 6 allows, prior to assembly in the optics-holder tube 4, the polishing of the end 14 of the fibre bundle. To this end, the end portion 1 of the fibre bundle 2 comprises a bare portion 9. Thanks to the most perfect possible surface condition of the end 14, the parasitic reflections at the input and output of the fibres are minimized and the quality of the signal is enhanced. The joining piece 6 is inserted in an adjusted manner into the optics-holder tube 4. On the side of the rear end 10 of the optical head, the fibre bundle 2 is fixed using a spot of suitable glue 11 (biocompatible and ensuring tightness) joining the sheath 12 of the fibre bundle 2, the rear surface 13 of the joining piece 6 and the optics-holder tube 4, the joining piece 6 being situated slightly retracted in the optics-holder tube. On the side of the bare end 9 of the fibre bundle 2, the joining piece 6 has an annular collar 16 retracted relative to the outside surface of the joining piece defining one end 17 which is narrow in diameter. An opening 18 is present in the optics-holder tube 4 intended to face the narrow end 17 of the joining piece 6 in order to be able to adjust the position of the joining piece 6 and introduce a second spot of suitable glue 20. This also allows the gluing to its periphery of an index adaptation plate 21, with plane and parallel surfaces, said plate being placed in contact with the end 14 of the fibre bundle 2 and the end 17 of the joining piece 6. The diameter of the plate 21 corresponds to the internal diameter of the optics-holder tube 4. The characteristics of the plate 21, its nature and thickness, are chosen in order to obtain a good compromise between the level of backscattering and sufficient resistance for mechanical integration. Its index is chosen to be very close to that of the core of the fibres. The plate 21 thanks to this index and the choice of its thickness makes it possible to minimize and reject from the focal plane, the reflection occurring at the distal end of the image guide by carrying out an index adaptation. In contact with the periphery of the plate 21 there is provided a tubular spacer 22 used to space by a given length a focussing optical block 3 (which is described hereafter in detail), followed in contact with a second tubular spacer 26 used to space an output window 30. In this front end part 19 of the optical head, the optics-holder tube 4 has an internal recessed annular collar 27, against which the rear surface of the spacer 26 can be supported. Similarly an annular collar 28 is provided in the internal surface of the spacer 26 against which is positioned the periphery of the rear surface of the output window 30. The end of the spacer 26 and the window 30 are flush with the end 19 of the optical head. The output window 30 is a plate with parallel and plane surfaces, having here also a thickness sufficient to ensure a good resistance during the mechanical insertion. It is glued at its periphery in contact with the spacer 26. When it is intended to come into contact with a tissue, the window is chosen in order to be chemically neutral. The window allows at the same time to realise an index adaptation relative to the observation site in the same manner as at the output of the fibre bundle 2, which produces a minimization of the reflection occurring on the analyzing surface. In the case of the observation of a biological tissue, an anti-reflection treatment in water can moreover be carried out in order to be better adapted to the index of the tissues, and thus to improve the image contrast. The optical system is according to the invention telecentric in the image space.

The assembly of the optical head is carried out in the following manner: the joining piece 6 is fitted onto the end portion of the optical fibre bundle having a bare end portion; this assembly is then inserted and adjusted in the optics-holder tube 4 conforming the opening 18 of said tube 4 with the narrow portion 17 of the joining piece 6; at the other end first optical path T1 of a principal beam centred on the optical axis of the system is represented as a full line and a second optical path T2 of a beam emerging from an optical fibre or group of fibres not situated on the optical axis as a dotted line. The beam emerging from the window 30 converges in an excitation focal point, for example PT1 or PT2, situated in a subsurface analysis plane XY. The signal backscattered by the excitation focal point then allows the same optical path in the reverse direction.

The detailed characteristics (curvature, position etc.) of the different lenses 31 to 37 according to a particular embodiment as well as of the plate 21 and of the output window 30 are given in Table 1 hereafter.

TABLE 1

(M = 1)

| | Surface | Type | Radius | Thickness | Class | Diameter |
|---|---|---|---|---|---|---|
| | OBJ | STANDARD | Infinite | −100 | | 0.7 |
| | STO | STANDARD | Infinite | 100 | | 92.55952 |
| 21 | 2 | STANDARD | Infinite | 0.5 | BK7 | 0.7 |
| | 3 | STANDARD | Infinite | 0.3 | | 0.9907993 |
| 32 | 4 | STANDARD | −0.8862573 | 0.8 | BF6 | 1.094269 |
| | 5 | STANDARD | −1.201577 | 0.2 | | 2 |
| 33 | 6 | STANDARD | 6.25473 | 0.8 | BK7 | 2.3 |
| | 7 | STANDARD | −2.246746 | 0.2 | | 2.3 |
| 34 | 8 | STANDARD | 2.819419 | 0.8 | BF6 | 2.3 |
| | 9 | STANDARD | Infinite | 0.4 | | 2.3 |
| | 10 | STANDARD | −2.12778 | 1 | BK7 | 2.3 |
| 31 | 11 | STANDARD | Infinite | 0 | | 2.3 |
| | 12 | STANDARD | Infinite | 1 | BK7 | 2.3 |
| | 13 | STANDARD | 2.12778 | 0.4 | | 2.3 |
| 35 | 14 | STANDARD | Infinite | 0.8 | BF6 | 2.3 |
| | 15 | STANDARD | −2.819419 | 0.2 | | 2.3 |
| 36 | 16 | STANDARD | 2.246746 | 0.8 | BK7 | 2.3 |
| | 17 | STANDARD | −6.25473 | 0.2 | | 2.3 |
| 37 | 18 | STANDARD | 1.201577 | 0.8 | BF6 | 2 |
| | 19 | STANDARD | 0.8862573 | 0.3 | | 1.117908 |
| 30 | 20 | STANDARD | Infinite | 0.5 | BK7 | 1.029353 |
| | 21 | STANDARD | Infinite | 0.08 | 1.330000 62.00000 | 0.7554534 |
| | 22 | STANDARD | Infinite | 0 | | 0.7049318 |
| | IMA | STANDARD | Infinite | | | 0.7049318 | of the optics-holder tube 4, the plate 21 is fitted on so that it comes into contact with the end 14 of the fibre bundle; then the spacer 22, the optical block 3, the spacer 26 and finally the window 30 are introduced; spots of glue 11 and 20 are applied in order to fix the joining piece 6 and the plate 21.

The optical block 3 comprises a set of lenses having the function of focussing an excitation beam into an excitation focal point situated in a subsurface analysis plane XY perpendicular to the optical axis. The choice of the position (in an extra-focal plane), the curvature and of an optimal anti-reflection treatment makes it possible to avoid the signal reflected by the lenses causing interference to the signal originating from the sample (the coupling of the reflected signal must not exceed 10–5 relative to the fibre output signal).

Figure 2:
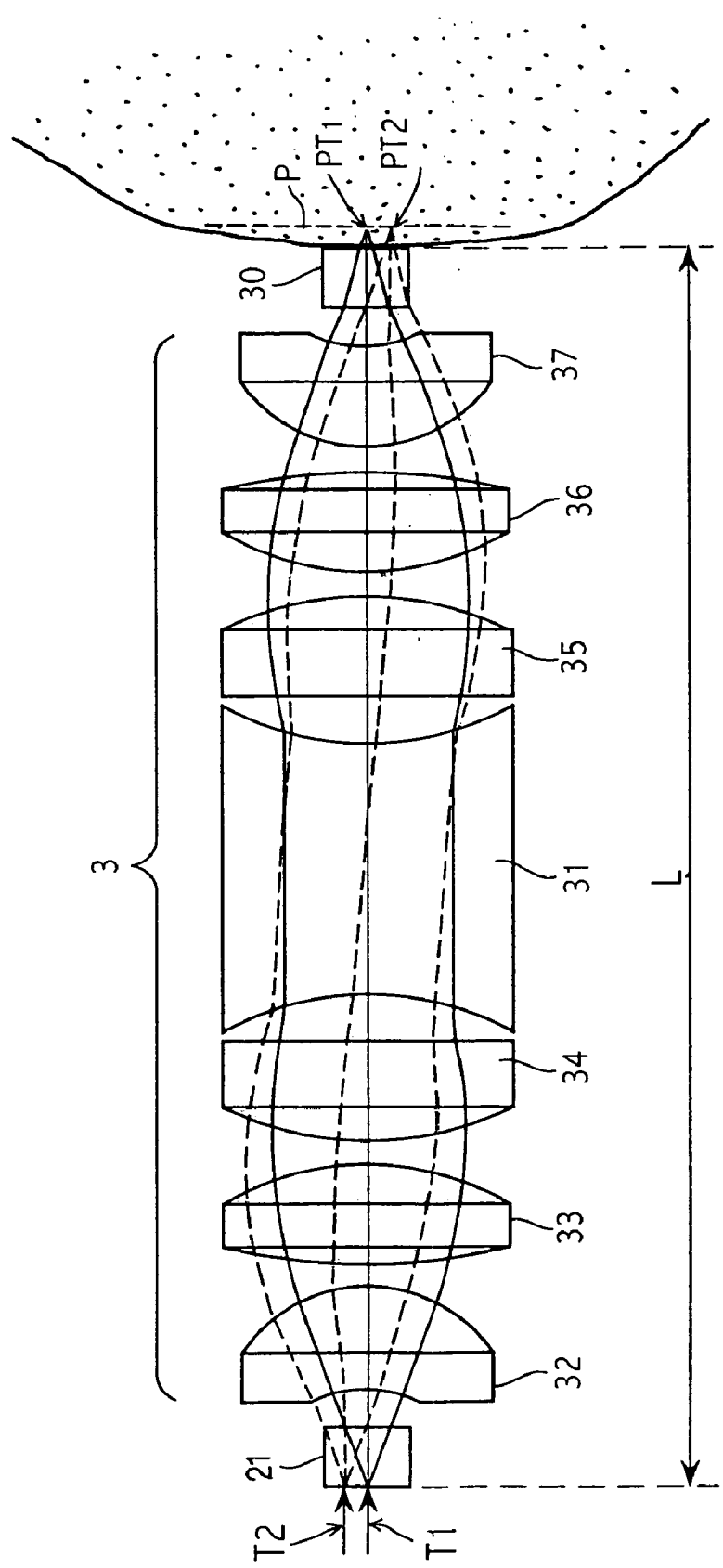
FIG. 2 is an optical diagram illustrating an embodiment of the focussing optical block with unitary magnification.

By way of example, FIG. 2 shows an optical block 3 with unitary magnification comprising symmetrically on either side of a bi-concave lens 31 of BK7, glass, beyond the plate 21: a meniscus 32 of SF6 glass, a bi-convex lens 33 of BK7 glass and a planoconvex lens 34 of SF6 glass, and upstream of the output window 30 a planoconvex lens 35 of SF6 glass, a bi-convex lens 36 of BK7 glass and a meniscus 37 of SF6 glass.

FIG. 2 shows diagrammatically the optical path of an excitation beam emerging from the optical fibre bundle. A The construction according to the invention can be miniaturized while allowing a very good quality signal, as shown by the characteristics hereafter, given by way of example, for an optical head having the characteristics which have just been described with reference to FIG. 1 and intended to be inserted into the instrument channel of an endoscope, and utilizing at the proximal end of the signal guide confocal imaging means comprising: a light source (for example a pulsed laser), scanning means for injecting the bundle produced fibre by fibre in addressed manner, means for time and spatial filtering of the backscattered signal, detection means, signal-processing means and image-display means, as described in particular in the International Application WO 00/16151.

Characteristics of an optical head according to the invention for a coloscope or gastroscope:
  Dimensions:
    2.5 mm external diameter for the optics-holder tube;
    a fibre bundle 2 for example of Sumitomo® trademark constituted by 30,000 fibres with a core diameter of 2.5 µm and of inter-core spacing of 4 µm or of Fujikura® trademark constituted by 30,000 fibres with a core diameter of 1.9 µm and inter-core spacing of 3.3 µm;
    an optical block 3 having 1.8 mm in diameter;

a length L (see FIG. 1) between the signal guide fibre output and the external surface of the output window 30 of 8.75 mm, with a front lens varying from 50 to 150 μm;

a total length comprising L and the rigid mechanical joining to the optical fibre bundle of 16.6 mm, compatible with the radius of curvature of the instrument channel of a standard coloscope (Rc=40 mm);

0.5 mm thickness for the index adaptation plate 21 and for the output window 30, sufficient during the mechanical insertion and allowing a backscattering level of the order of $3.10^{-4}$.

Operating temperature: 37° C.

Image quality image quality close to the diffraction limit; the WFE, "wave front error", throughout the field is of the order of $\lambda/30$ at the centre of the field to $\lambda/20$ at the edge of field; this excellent image quality ensures a good return coupling in the excitation fibre (~90%);

MTF (modulation transfer function): this corresponds to the relative intensity as a function of the spatial frequency. The cut-off frequency is defined by $1/(2d)$ where d corresponds to the inter-core distance of the fibres, and is expressed in cycles/mm. Here, with an inter-core distance of 4 μm, the cut-off frequency is 125 cycles/mm. The MTF allows evaluation of the quality of the image by comparing the curve to that of the diffraction limit, and using the criterion according to which the contrast must be 0.5 (value of the relative intensity given by the curve) at the maximum spatial frequency of the device, at a rate of 125 cycles/mm in the present case. The result obtained here is effectively close to the diffraction limit, having a contrast of 0.75 at the spatial frequency of 125 cycles/mm, therefore ensures a very good image quality;

Encircled energy: this allows evaluation of the lateral resolution that can be expected, by evaluating the percentage of energy contained in a diameter. In order to resolve a spot with a diameter of ϕ, 50% of the minimum energy must be contained in this diameter. In the present case, 50% of the energy originating from the object point is encircled in a diameter of 1.5 μm, whatever its position in the field. 50% of the energy originating from an optical fibre in the signal guide (with a core diameter of 2.5 μm) is therefore encircled in a diameter of 4 μm.

Curvature of field, distortion: The image is curved from 31 μm to 35 μm between the centre and the edge of the field. The residual curvature of field is very low (of the order of 2 μm), as well as the distortion (of the order of 0.8%).

Transmission on a path: of the order of 0.97%.

Thus, the solution proposed according to the invention can be effectively miniaturized and makes it possible to obtain a very good quality image having an expected lateral resolution (namely 4 μm) and to optimize the signal-to-noise ratio by minimizing the parasitic reflection at the image guide output, by optimizing the return coupling level and the transmission of the system. This solution resolves the problem posed and offers the advantages of simplicity of assembly and low cost.

Figure 3:
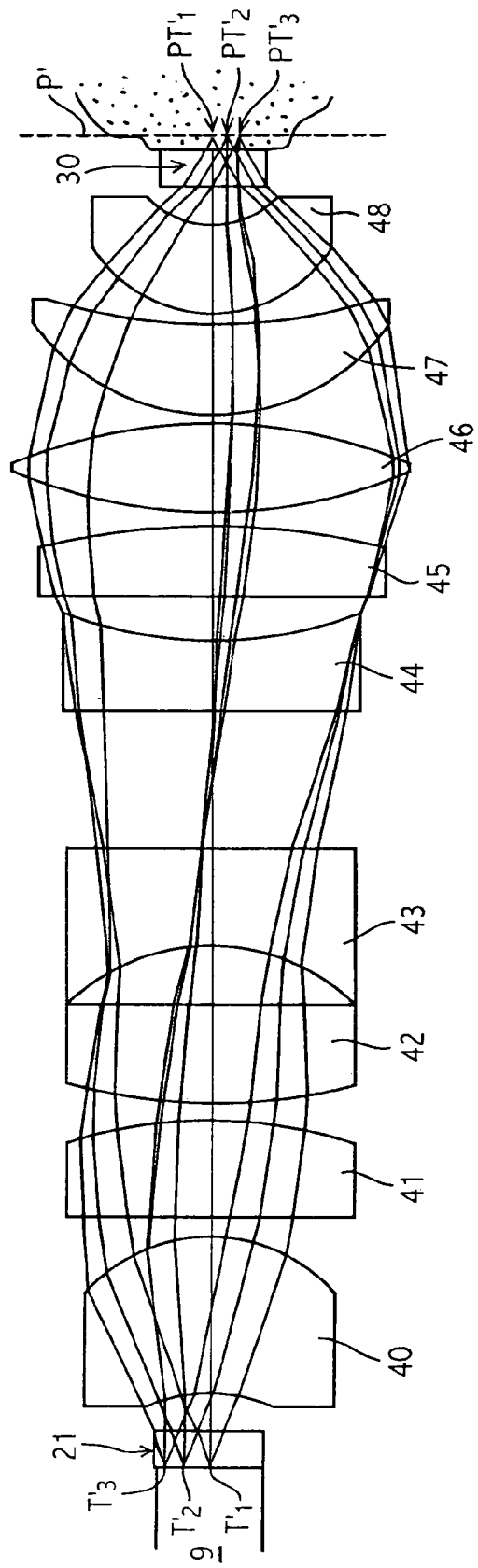
FIG. 3 is an optical diagram illustrating an embodiment of the focussing optical block with non-unitary magnification.

It goes without saying that variants of the invention are possible, in particular FIG. 3 shows a focussing optical block 3 with 0.5 magnification (the same references are used for the elements shared with FIG. 1). Beyond the index adaptation plate 21 there are arranged successively a meniscus 40 of SF6 glass, a planoconvex 41 of BK7 glass, a planoconvex 42 of SF6, a planoconcave 43 of BK7, a planoconcave 44 of BK7, a planoconvex 45 of SF6, a bi-convex lens 46 of BK7, a meniscus 47 of SF6 and a meniscus 48 of SF6. As in FIG. 2, there are represented here three optical paths emanating from a different fibre of the bundle: $T'_1$, centred on the optical axis, forming a focussing point $PT'_1$ in a subsurface plane P', and $T'_2$ and $T'_3$, non-centred marginal rays forming respectively a focusing point $PT'_2$ and $PT'_3$ in the plane P'.

The detailed characteristics according to a particular embodiment (curvature, position etc.) of the different lenses 40 to 48 as well as the plate 21 and the output window 30 are given in Table 2 hereafter.

TABLE 2

(M = 0.5)

|    | Surface | Type     | Radius     | Thickness | Class | Diameter   |
|----|---------|----------|------------|-----------|-------|------------|
|    | OBJ     | STANDARD | Infinite   | −100      |       | 0.7        |
|    | STO     | STANDARD | Infinite   | 100       |       | 92.55952   |
| 21 | 2       | STANDARD | Infinite   | 0.3       | BK7   | 0.7        |
|    | 3       | STANDARD | Infinite   | 0.3       |       | 0.8744796  |
| 40 | 4       | STANDARD | −0.8862573 | 1.3       | BF6   | 1.044886   |
|    | 5       | STANDARD | −1.201577  | 0.15      |       | 2          |
| 41 | 6       | STANDARD | 6.25473    | 0.8       | BK7   | 2.3        |
|    | 7       | STANDARD | −2.246746  | 0.15      |       | 2.3        |
| 42 | 8       | STANDARD | 2.819419   | 0.8       | BF6   | 2.3        |
|    | 9       | STANDARD | Infinite   | 0.5       |       | 2.3        |
| 43 | 10      | STANDARD | −2.12778   | 0.8       | BK7   | 2.3        |
|    | 11      | STANDARD | Infinite   | 1.1       |       | 2.3        |
| 44 | 12      | STANDARD | Infinite   | 0.6       | BK7   | 2.167773   |
|    | 13      | STANDARD | 2.12778    | 0.35      |       | 2.38508    |
| 45 | 14      | STANDARD | Infinite   | 0.6       | BF6   | 2.529293   |
|    | 15      | STANDARD | −2.819419  | 0.1       |       | 2.774485   |
| 46 | 16      | STANDARD | 2.246746   | 0.7       | BK7   | 3.173711   |
|    | 17      | STANDARD | −6.25473   | 0.1       |       | 3.180204   |
| 47 | 18      | STANDARD | 1.201577   | 0.7       | BF6   | 2.856758   |
|    | 19      | STANDARD | 0.8862573  | 0.1       |       | 2.636245   |
| 48 | 20      | STANDARD | Infinite   | 0.7       | BF6   | 1.924121   |
|    | 21      | STANDARD | Infinite   | 0.3       |       | 1.064745   |
| 30 | 22      | STANDARD | Infinite   | 0.3       | BK7   | 0.85978848 |

TABLE 2-continued (M = 0.5)

| Surface | Type | Radius | Thickness | Class | Diameter |
|---|---|---|---|---|---|
| 23 | STANDARD | Infinite | 0.08 | 1.330000 62.00000 | 0.5069504 |
| 24 | STANDARD | Infinite | 0 | | 0.3947683 |
| IMA | STANDARD | Infinite | | | 0.3947683 |

The non-unitary magnification, in this case 0.5 from the distal end of the image guide up to the analysis plane in this example of use, makes it possible to obtain:

a better lateral resolution (PSF of 0.75 µm for an extended object with a diameter equal to the core diameter of a fibre (1.9 µm), compared with 1.4 µm for an optical head with unitary magnification).

A better axial resolution (of the order of 5 µm compared with 10 µm for the optical head with unitary magnification)

A lager illumination numerical aperture (of the order of 0.9 compared with 0.42 for the optical head with unitary magnification), and as a result a more contrasted image.

Figure 4:
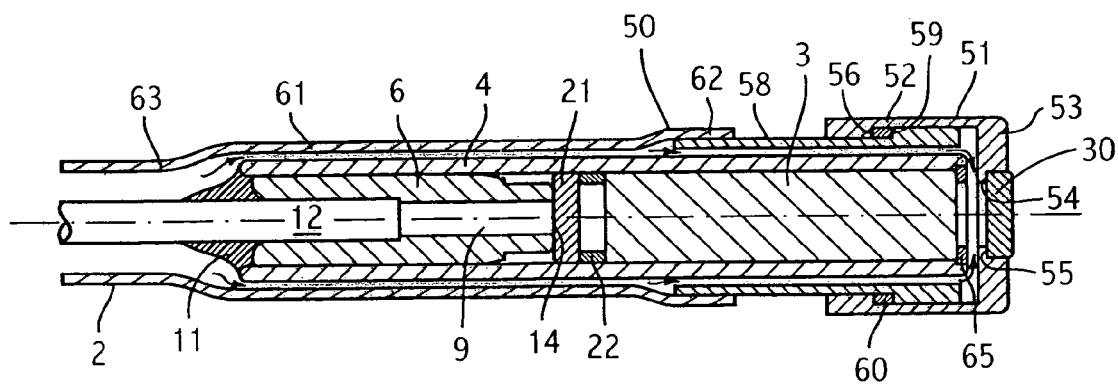
FIG. 4 is a cross-section view similar to FIG. 1 illustrating an embodiment of an optical head with adjustable depth of the field.

FIG. 4 shows another embodiment of an optical head according to the invention comprising hydraulic-type means for varying the depth of the analysis plane P. The elements similar to those in FIG. 1 have the same references. The head differs from that in FIG. 1 in that the window 30 is carried by a cap, having the overall reference 50, which is fitted onto the optical head. This cap comprises an end portion 51 with a skirt 52 and a front wall 53 in which is fitted an opening 54 with an annular flange 55 adapted for receiving the window 30, the periphery of the latter being glued onto the flange 55 with a suitable glue. The external diameter of this end portion 51 can be approximately 3 mm, a dimension compatible with the instrument channel of an endoscope. The skirt 52 is fitted onto a so-called intermediate tubular portion 58 of the cap 50, coupling means being provided between theses two portions comprising on the internal surface of the skirt 52, a recessed annular flange 56, and on the external surface of the intermediate portion 58 a collar 59, a compressible ring seal 60 being arranged between said portions, ensuring the tightness of the coupling. Finally, the cap 50 comprises a rear portion 61, intended for coupling to an air supply, the diameter of the front end of which 62 is enlarged in order to be coupled onto the rear end of the intermediate portion 58 and the rear diameter 63 is narrow in order to be adapted to the diameter of the optical fibre bundle 2. The cap 50 has an internal diameter, which is globally greater than the external diameter of the optics-holder tube, in such a manner that a space is arranged between the cap 50 and the optical head which is provided for connection to the air supply. Thus, according to the invention, the adjustment of the position of the subsurface focal plane is carried out not by modifying the position of the lenses inside the optical block 3 but by modifying the position of the window 30 relative to said optical block 3, thanks to a mobile cap 50 actuated pneumatically, carrying said window.

The head which has just been described also differs from that described with reference to FIG. 1, in that no spot of glue is provided such as 20 in FIG. 1 for fixing the end of the joining piece 6. The fixing is carried out here using the spot of glue 11 behind the head and a ring 65 fixed at the end of the optics-holder tube 4 against a collar.

The invention claimed is:

1. Miniaturized optical head provided for equipping the distal end of a flexible optical fibre bundle (2), said optical head being intended to come into contact with an analyzing surface and comprising optical means (3) for focussing an excitation signal coming out from said fibre bundle into a so-called excitation focal point situated at a given depth beneath the analyzing surface and for sampling a signal backscattered by the excitation focal point which is carried back by said fibre bundle, characterized by an optics-holder tube (4) circular in section wherein are inserted on one side the distal end portion (1) of the fibre bundle (2) and on the other the optical means, the latter comprising a plate (21) placed in contact with the end (14) of the fibre bundle the index of which is close to that of the fibre core and a focussing optical block (3), an output window (30) being moreover intended to come into contact with the analyzing surface and adapted to produce an index adaptation in order to eliminate parasitic reflection occurring on the analyzing surface.

2. Optical head according to claim 1, characterized in that the optical block comprises a set of lenses, each lens being positioned in an extra-focal plane making it possible to avoid the signal reflected by the lenses causing interference to the signal originating from the sample.

3. Optical head according to claim 1, characterized in that the optical block comprises a set of lenses, each lens having an optimal anti-reflection treatment making it possible to avoid the signal reflected by the lenses causing interference to the signal originating from the sample.

4. Optical head according to claim 1, characterized in that the optical block comprises a set of lenses, each lens have a curvature adapted in order to avoid the signal reflected by the lenses causing interference to the signal originating from the sample.

5. Optical head according to claim 1, characterized in that the window (30) is inserted at the end of the optics-holder tube (4), a tubular spacer (26) being arranged between the optical block (3) and said window (30).

6. Optical head according to claim 5, characterized in that the periphery of the window (30) is placed abutting against a collar arranged in recess inside the spacer (26).

7. Optical head according to claim 5, characterized in that the tubular spacer (26) is placed abutting against a collar (27) arranged in recess inside the optics-holder tube.

8. Optical head according to claim 1, characterized in that the window (30) is carried by a mobile cap (50) coupled onto the end of the optical head, means being provided for displacing said cap in such a manner as to vary the focal plane of visualization of a given depth.

9. Optical head according to claim 8, characterized in that the mobile cap (50) comprises an end portion (51) with a front surface (53) in which is arranged an opening for the window (30), said end portion (51) being coupled to an intermediate portion (58) of the mobile cap (50) and a compressible seal (60) being arranged at the level of the coupling.

10. Optical head according to claim 9, characterized in that the window (30) is glued against a collar (55) arranged for this purpose in the opening of the end portion (51).

11. Optical head according to claim 8, characterized in that a space is arranged between the mobile cap (50) and the optical head in communication with an air supply, the adjustment of the air supply allowing displacement of said cap and therefore of the position of the output window (30).

12. Optical head according to claim 1, characterized by a mobile optical means provided in the optical block adapted to be displaced axially.

13. Optical head according to claim 12 characterized in that the displacement is carried out using a piezo-electric motor.

14. Optical head according to claim 1 characterized by an optical means in the optical block possessing a radius of curvature which can be modified in order to change its focal distance and therefore the depth of the observation plane.

15. Optical head according to claim 14, characterized in that the optical means is a liquid optical means.

16. Optical head according to claim 1, characterized by the presence of a tubular joining piece (6) arranged about the end portion (1) of the fibre bundle (2), the end (14) of the fibre bundle being flush with the end of said joining piece.

17. Optical head according to claim 16, characterized in that the optical fibre bundle (2), comprising a sheath (12), in its portion surrounded by the joining piece (6) has a bare end portion (9).

18. Optical head according to claim 16, characterized in that the joining piece (6) is situated somewhat retracted inside the optics-holder tube (4) in such a manner that a spot of glue (11) can be arranged in contact with the rear end (13) of the joining piece (6), the rear end of the optics-holder tube (4) and the sheath (12) of the fibre bundle (2).

19. Optical head according to claim 16, characterized in that the joining piece (6) on the side of the index adaptation plate (21) comprises an end with a narrow diameter (17) facing which is arranged an opening (18) in the optics-holder tube (4) and said plate (21) having an external diameter corresponding to the internal diameter of the optics-holder tube (4) in such a manner that a spot of glue (20) can be arranged in contact with said end of joining piece (17), the periphery of said plate (21) and the optics-holder tube (4).

20. Optical head according to claim 1, characterized by a tubular spacer (22) arranged between the index adaptation plate (21) and the focussing optical block (3).

21. Use of the optical head according to claim 1 in a confocal imaging endoscope.

22. Use of the optical head according to claim 21 in a confocal imaging endoscope using a bundle of optical fibres scanned one by one at the proximal end of said bundle.

* * * * *